United States Patent [19]

Severy

[11] 4,378,213

[45] Mar. 29, 1983

[54] USE OF CYANOACRYLATE COMPOUNDS FOR DENTAL MODELING

[75] Inventor: Steven E. Severy, Anaheim, Calif.

[73] Assignee: MDS Products Company, Inc., Calif.

[21] Appl. No.: 182,981

[22] Filed: Sep. 2, 1980

[51] Int. Cl.³ .............................................. A61C 11/00
[52] U.S. Cl. ................................... 433/213; 433/228;
264/16; 106/35
[58] Field of Search ................ 433/228, 24, 213, 180,
433/9, 223, 217; 264/129, 134, 16, 17, 18, 19;
106/35; 260/998.11

[56] References Cited

U.S. PATENT DOCUMENTS

| | | | |
|---|---|---|---|
| 3,250,002 | 5/1966 | Collito | 433/228 |
| 3,518,762 | 7/1970 | Takeuchi | 433/228 |
| 3,527,841 | 9/1970 | Wicker et al. | 526/298 |
| 3,540,126 | 11/1970 | Chang et al. | 106/35 |
| 3,663,501 | 5/1972 | Adams et al. | 433/228 |
| 3,896,077 | 7/1975 | Leonard et al. | 526/298 |
| 3,949,478 | 4/1976 | Schinhammer | 433/24 |
| 4,012,840 | 3/1977 | Takeuchi et al. | 433/217 |
| 4,170,585 | 10/1979 | Motegi et al. | 526/298 |
| 4,180,911 | 1/1980 | Bullock | 106/35 |
| 4,180,913 | 1/1980 | Takeuchi et al. | 260/998.11 |
| 4,288,472 | 9/1981 | Jorgensen | 264/16 |

*Primary Examiner*—Gene Mancene
*Assistant Examiner*—John J. Wilson
*Attorney, Agent, or Firm*—Kenneth E. Darnell

[57] ABSTRACT

Methods for performing operations on a die or dental model including the filling in or "basing up" of voids, deep areas and undercuts; the indexing and investment soldering of dental crowns from a die model; and aid in the fabrication of porcelain jacket crowns and the like; the invention particularly contemplates the use of a cyanoacrylate compound to effect said methods. According to the present methods, a high viscosity cyanoacrylate base material, typically the methyl or ethyl ester of the cyanoacrylate is deposited on the die model in the areas which are to be based up, blocked out or the like, an activator or accelerator compound such as an aromatic amine or the like being then sprayed, preferably in an atomized mist form, onto the deposited base material. The base material rapidly cures to a hardened mass upon which further operations, such as cutting and shaping, if necessary, can immediately be performed, thereby resulting in a substantial reduction of time and labor conventionally required to perform such operations.

9 Claims, 12 Drawing Figures

USE OF CYANOACRYLATE COMPOUNDS FOR DENTAL MODELING

BACKGROUND OF THE INVENTION

1. Field of the Invention

The invention relates to methods for performing a variety of operations on a die or dental model using cyanoacrylate compounds. In particular, the methods include the use of cyanoacrylate compounds to base up and block out voids, deep areas, undercuts, and the like on a die model as well as to index dental crowns on a die model for investment soldering and to aid in fabricating porcelain jacket crowns and unbreakable die models.

2. Description of the Prior Art

Die models are commonly used in dental laboratories for a number of well-known dental fitting and fabrication purposes. Typically, a model is formed of a gypsum or epoxy material by casting from a negative impression mold of the teeth made in a dentist's office. The die model is then used to fabricate, size, and pre-fit dental appliances such as crowns, porcelain jacket crowns, indexed multiple crowns and the like. In order for these appliances to fit properly in the mouth, the model must accurately represent the structural condition of the teeth and must be free of flaws which often result due to the nature of the tooth preparation, impression process and of the casting process. Further, dental models must often be modified to reflect the structural condition of the teeth which should exist at the time of fitting of an appliance even though such a condition did not exist at the time the impression mold was made. Exemplary of such flaws and conditions which must be corrected on the model are bubble voids which occur in the casting process, undercuts which occur usually in the tooth preparation process, and deep areas which often result on removal of decay and which are not filled in on the tooth prior to impression molding. These voids, undercuts, and deep areas must be filled in, blocked out, or based up as necessary in order to produce a model of the tooth which is proper for seating or fitting a crown or other appliance on the model of the tooth without resistance. Once the model itself has been properly prepared, operations such as the indexing of two or more dental crowns and subsequent transfer to a solder investment are often required. In some situations, the model itself must be unbreakable in order to index a bridge or precision partial abutment.

Dental technicians have developed considerable skills in preparing die models for use and for working with the die models once prepared. However, the materials and techniques heretofore available to the technician have inherently resulted in lost time due not only to material failures but also to the lengthy time periods required for adequate solidification or curing of a material before subsequent operations can be performed on the model. In order to perform these operations both efficiently and effectively, the technician requires a material which can conveniently be used with a minimum of cleaning of the work area, which requires a minimum of time for setting or curing, which has acceptably low shrinkage, and which is not susceptible to melt-through when contacted with molten wax. Prior materials used by the dental technician have failed to meet with all of the above requirements even though substantial investments of time and resources have been directed toward the indentification and development of a material capable of exhibiting the stated characteristics. Traditionally, various waxes and similar compounds have been used and are now in widespread use in spite of the many shortcomings of these materials. In use, a wax has been melted and flowed into an undercut or the like, the wax then being smoothed out with a heated instrument. Specialized equipment, such as a heat source and the like, is thus required. The necessity for such equipment adds expense to the operation of a dental laboratory and thus requires additional maintenance for the equipment and effort in maintaining the work area in an orderly condition. When subsequent operations require the application of additional molten wax to the model which has been prepared with a wax material, the subsequently applied wax often adheres to the wax used to prepare the model, even though a lubricant is conventionally applied to the prepared model. When the subsequently applied wax adheres to or flows through or into the wax used to prepare the model, the wax tooth model sculpted from the subsequently applied wax invariably breaks when removed from the model, thereby resulting in a significant loss of time and labor. Such problems are also a cause of undeniable and previously unavoidable frustration to the technician. This most commonly used of die preparation materials also presents clean-up problems which occur during the finishing and polishing of cast crowns and the like. In such situations, should the technician fail to remove any adhering wax, processing heat melts the wax or similar dental compound to the inside of the crown, thereby requiring additional labor cost to clean both the die model and the crown.

The use of a base-up material such as a gypsum product, the material from which most die models are cast, requires water soaking of the die model to facilitate adhesion of the base-up material, the time delays thus inherent in such a process being usually unacceptable to an orderly progression of work within a dental laboratory. Further, such a material does not adhere well to an unsoaked model and does not set sufficiently rapidly to prevent undesirable flow of the material into other areas of the model, thus requiring removal of the unwanted material or scrapping of the ruined model. Certain other materials used for preparation of dental models require the use of expensive equipment such as ultraviolet radiation generators which are necessary for curing, these ultraviolet cured materials being much more expensive than other candidate materials. Due to the potential for hazard in the use of ultraviolet radiation, many dental technicians hesitate to use a material if so cured. Polymeric materials previously used as base-up materials have required mixing of liquids and powders, the mixtures requiring substantial time to sufficiently thicken to allow application to the model. Once applied, these materials do not rapidly cure to a hard set and, when set, exhibit unacceptable shrinkage of up to 15%. Use of these polymeric materials requires a substantial and unavoidable cleaning of the work area.

The present invention contemplates the use of materials which exhibit all of the characteristics referred to above as being important to the preparation of a dental model and to the performance of various operations on a prepared model. In particular, the invention provides an inexpensive material which requires no extraordinary use precautions, which requires no mixing or after-use clean-up, which sets in a minimum of time to a hardened condition not susceptible to wax flow-through or adherence, and which does not exhibit an unacceptable degree of shrinkage. The methods according to the present invention involve the use of high viscosity cyanoacrylate compounds which are hardened through the use of an accelerator, particularly by the application of an atomized mist of an accelerator, whether or not in a volatile solvent, to the cyanoacrylate compound previously positioned on the model. Substantial savings of time and labor result through practice of the present methods, certain heretofore unobtainable advantages to be hereinafter described being realized according to the teaching of the present invention.

BRIEF DESCRIPTION OF THE DRAWINGS

FIG. 6 is an idealized elevational view of a single tooth of a die model wherein the tooth model has a bubble void which is to be filled in;

DESCRIPTION OF THE PREFERRED EMBODIMENTS

Figure 1:
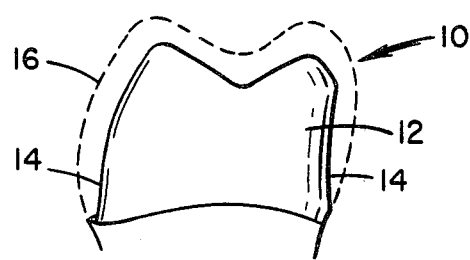
FIG. 1 is an idealized elevational view of a single tooth of a die model after preparation.

Several methods constituting the present invention particularly contemplate a new use of compounds previously used to bond structural elements together, the compounds being generally referred to as cyanoacrylates and including activators or accelerators therefor which are typically classed as Lewis bases. Such materials are described inter alia in U.S. Pat. Nos. 3,903,055; 3,992,515; 3,223,083; 3,264,249; 3,559,652; 3,839,065; 3,940,362; and 4,042,442; the disclosures of which are incorporated hereinto by reference. U.S. Pat. No. 3,903,055 is exemplary in that the patent discloses the causation of accelerated setting of cyanoacrylate monomers and comonomers through the use of an amine catalyst, the catalysis typically polymerizing 2-cyanoacrylic acid. In particular, isobutyl cyanoacrylate is polymerized by N,N-dimethyl-p-toluidine to cement brackets to the teeth in a proposed "in-mouth" usage. The cyanoacrylates can further be thickened in a variety of ways, such as through addition of organic fillers as disclosed in U.S. Pat. Nos. 2,794,788; 3,836,377; 3,692,752; and 4,102,945; or through addition of inorganic fillers as disclosed in U.S. Pat. Nos. 3,663,501 and 3,607,542; the disclosures of these patents being incorporated hereinto by reference. Certain cyanoacrylate compositions are disclosed in U.S. Pat. No. 3,652,930, the disclosure of which is incorporated hereinto by reference, this patent disclosing inter alia the polymerization of methyl or ethyl esters of the cyanoacrylate by an aromatic amine which can be carried in a highly volatile acetone solvent.

Preferred accelerator compounds according to the invention include aromatic amines such as N,N-dimethyl-p-toluidine and the homologs thereof and phenylethylethanolamine and the homologs thereof. These accelerators can be carried by a volatile solvent such as trichloroethane. Preferred base materials include ethyl cyanoacrylate, methyl cyanoacrylate, n-butyl cyanoacrylate and the like. These materials have not previously been proposed for use in the preparation of dental models or in the fabrication of dental appliances using such dental models. The advantages which accrue to the dental laboratory technician from the use of cyanoacrylate compounds as disclosed herein have not been available prior to the present invention in spite of intensive interest and research efforts in the field.

The invention particularly contemplates the use of a high viscosity cyanoacrylate which remains positioned on the dental model at the location where placed, that is, the material does not readily flow. The cyanoacrylate, which is referred to as a "base" is typically placed on an area of the model through use of an applicator as will be described hereinafter to fill in, base-up or block out a flaw, the base cyanoacrylate then being contacted with an accelerator which immediately initiates cure or hardening of the base material. The base material typically hardens adequately for further use of the model within a period of two to three minutes. The accelerator is typically applied in the form of a fine, atomized mist from a squeeze bottle or similar applicator which allows ready control of the quantity of accelerator applied to the base and of the location of application of the accelerator. Since both the base and the accelerator can be dispensed directly from storage containers of the compounds onto the model, the necessity for mixing and cleaning is eliminated. The accelerator can be carried by a volatile solvent which assists in dispensing said accelerator, the solvent being vaporized almost instantaneously when dispensed from an applicator such as an aerosol container.

Referring now to the drawings, and particularly to FIG. 1, a model of an ideal preparation on a tooth which is to receive a crown is shown generally at 10. Both the tooth which is to ultimately receive the crown and the model tooth 12 on a die model must have a desired design, such is known and typically approved by the American Dental Association and the various state dental examiner's boards. The preparation on the model tooth 12 must have walls or sides 14 which are essentially parallel or nearly parallel as in a slightly upwardly tapering "tepee" or similar shape. The crown or other dental appliance can then be fitted or seated on the model tooth 12 without resistance. The fitted crown is thus subsequently precisely located on the actual tooth. The original outline of the tooth can be seen at 16 in phantom. In practice, dental models must be "prepared", that is, flaws which often occur due to errors or intentional omissions must be corrected on the dental model. These flaws range from voids which occur in the casting of the model to undercuts and the like which can result from the manner of original tooth preparation.

Figure 2:
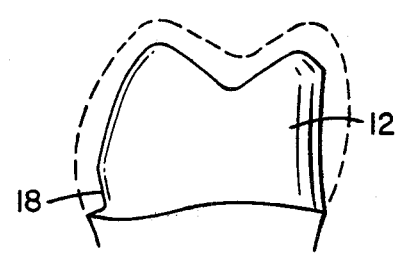
FIG. 2 is an idealized elevational view of a single tooth of a die model wherein the tooth model has an undercut which is to be blocked out to cause the model tooth to conform to the configuration of the model tooth of FIG. 1.

As can be seen in FIG. 2, an undercut at 18 on one of the walls 14 of the tooth 12 must be filled in or "based-up" so that a crown can seat or fit on the model tooth 12 without resistance. The walls 14 must be parallel or nearly so as aforesaid. The undercut 18 is based up by applying a high viscosity cyanoacrylate compound such as by the technique illustrated in FIG. 11, an accelerator being then applied to the compound as illustrated in FIG. 12 and as will be described in greater detail hereinafter. The hardened cyanoacrylate readily adheres to the model tooth 12 and can be readily shaped if necessary by cutting such as with a sharp modeling knife.

Figure 3:
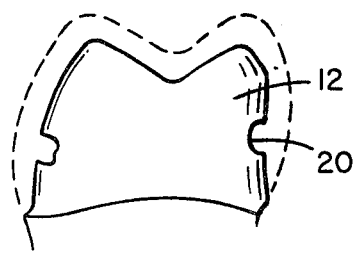
FIG. 3 is an idealized elevational view of a single tooth of a die model wherein the tooth model has undercut areas which represent areas on a tooth from which decay was removed, the undercut areas being necessarily blocked out on the model tooth to conform to the configuration of the model tooth of FIG. 1.
Figure 4:
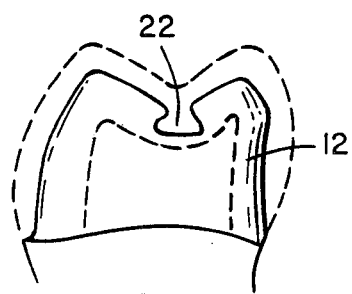
FIG. 4 is an idealized elevational view of a single tooth of a die model wherein the tooth model has a deep area which resulted from the removal of decay from the tooth from which the model was made, the deep area being based up on the tooth model in order that the nerve in the actual tooth will be insulated from a crown or other appliance made from the die model.
Figure 5:
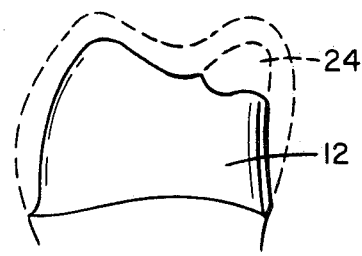
FIG. 5 is an idealized elevational view of a single tooth of a die model wherein the tooth model has a missing area which is to be filled in to cause the model tooth to conform to the configuration of the model tooth of FIG. 1.

Referring now to FIGS. 3, 4 and 5, areas are seen on the model tooth 12 which usually result from the taking of an impression after removal of decay from an actual tooth but without filling of the resulting cavity. It is to be understood that such a cavity can be conventionally filled by the dental practitioner prior to taking the impression from which a negative mold of the teeth is made. However, a cavity in the tooth is often left unfilled until after the impression is taken with the result that the model tooth 12 has undercut areas such as are seen at 20 in FIG. 3, a deep area such as is seen at 22 in FIG. 4, or a missing area such as is seen at 24 in FIG. 5. These areas 20, 22 or 24 must then be based-up or blocked out on the die model which is made from the impression mold. According to the present invention, the areas 20, 22 or 24 are filled in by deposition of the cyanoacrylate, such as ethyl cyanoacrylate, into or onto said areas in order to completely fill or build up the area to the desired contours, the cyanoacrylate then being sprayed with the accelerator, preferably in a fine, atomized mist, to cause rapid hardening of the cyanoacrylate. The model tooth 12 can then be worked with within a very short time as necessary.

Figure 6:
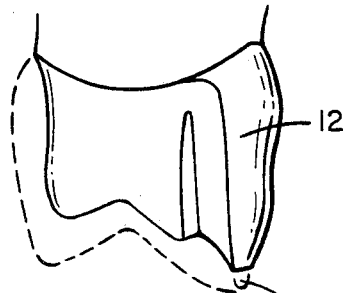

Referring now to FIG. 6, the model tooth 12 is seen to have been formed with a negative void or bubble 26 or other negative artifact which results from the casting process. The bubble 26 can be readily filled with the cyanoacrylate compound and contacted with the accelerator as described herein. Application of the cyanoacrylate compound can occur by a variety of techniques, including the deposition of the cyanoacrylate compound onto a blade or other sharp instrument and application to the bubble void. Such an application technique is particularly suited to small bubbles 26 which are too small to accommodate even a single drop of cyanoacrylate compound from a drop-wise dispenser.

Figure 7:
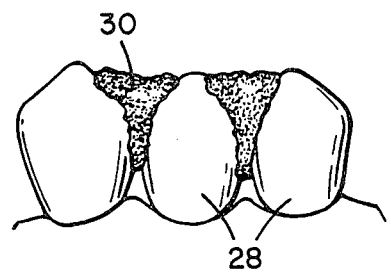
FIG. 7 is an idealized view of a series of indexed crowns which are bound together according to the invention prior to soldering.

In FIG. 7, an illustration is seen of the indexing of two or more dental crowns 28 on a die model. The dental crowns 28 must be indexed on the die model prior to soldering together of the crowns. When the crowns 28 are properly indexed on the die model, the crowns must rigidly stick together when transferred to the solder investment so that the relationship between the crowns will not change. The material used to hold the indexed crowns 28 together during this processing must exhibit a minimum of shrinkage and must adequately stick to the crowns. Further, once the crowns are placed into the soldering investment, the material must burn off cleanly without leaving a residue which can act as an anti-flux to prevent the solder from bonding or welding the crowns together. In effect, the material must be a fluid which becomes solid within a reasonable time and which, when solidified, exhibits the characteristics thus noted. As seen in FIG. 7, cyanoacrylate compound cement 30 is disposed between the crowns 28 and cured by contact with the accelerator as described herein, the crowns 28 are thus caused to rigidly adhere to each other within a matter of two or three minutes, the indexed and joined crowns being then soldered with complete burn off of the hardened compound and minimal shrinkage. According to a preferred method, the crowns 28 are placed on the die model for indexing and one application of accelerator is made to the crowns. The cyanoacrylate compound is then applied both between the crowns 28 which are to be joined and on top of the crowns. Accelerator is then again applied. A complete hardened cure occurs in less than five minutes, a time saving previously unavailable to the dental technician.

Figure 8:
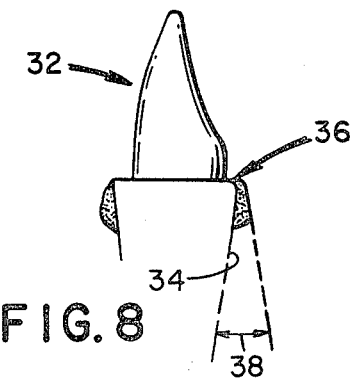
FIG. 8 is an idealized side elevational view of a single tooth of a die model illustrating the blocking out of undercut areas below the margin of the model tooth.

Fabrication of a porcelain jacket crown requires that a platinum foil be first adapted to a die model and then subsequently removed. As seen in FIG. 8, model 32 used for such a fabrication process must not have undercut areas, such as at 34 below margin 36. Such undercut areas 34 must be blocked out prior to adaptation of the foil to the model 32 in order to prevent distortion of the foil on removal of said foil from the model. The cyanoacrylate compound according to the present invention will flow only to the margin angle shown at 38 and will stop at said angle without overflow due to the viscosity of the compound. Accordingly, little or no carving of the hardened cyanoacrylate is necessary.

Figure 9:
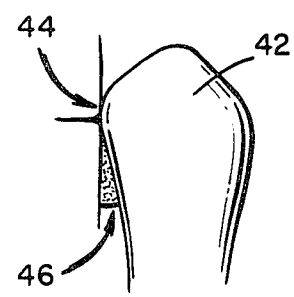
FIG. 9 is an idealized elevational view of a single tooth of a die model wherein an undercut area on the die model is blocked out below the height of contour in order to facilitate fabrication of dental appliances such as a removable partial clasp.

FIG. 9 illustrates the blocking out of an undercut area 40 on a model 42 as one operation in the fabrication of a removable partial denture. The undercut area 40 below the height of contour where a clasp of the denture will be placed must be blocked out on the model 42 in order to control the depth or intensity of the retention of the clasp. When the cyanoacrylate compounds described herein are used to fill the undercut area 40, the compound flows to the height of contour at 44 and not over said height of contour due to the viscosity of the compounds. Misting of the compound with the accelerator as described herein results in an extremely rapid set of the compound and allows the technician to continue with fabrication of the partial denture with a minimum of delay.

Figure 10:
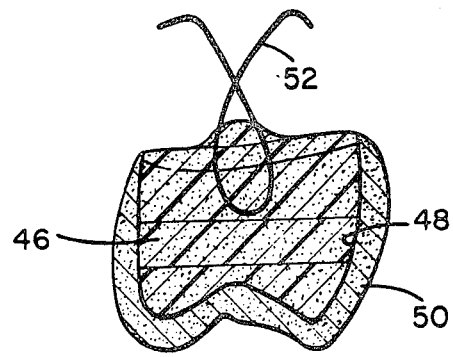
FIG. 10 is an idealized elevational view in section illustrating the molding of an unbreakable die model tooth within a crown.

Referring now to FIG. 10, a multiple layer unbreakable die model 46 is seen. The die model 46 is typically fabricated either after the crowns are re-indexed in the mouth and prior to soldering, or for the construction of a precision partial denture. Cavity 48 of a crown 50 is lubricated with an oleaginous lubricant such as is known in the art and any undercuts (not shown) are blocked out. The cavity 48 is a negative mold of a previously prepared die model. The cavity 48 of the crown 50 is then preferably sprayed with accelerator and a cyanoacrylate compound according to the invention is deposited within the cavity 48 of the crown 50 to a depth of approximately one-third the height of said cavity. The accelerator is then spread over the exposed surface of this first layer of compound, a second layer of cyanoacrylate compound being then deposited into the cavity over said first layer to a total depth of approximately two-thirds the height of the cavity. The accelerator is then sprayed over the exposed surface of the second layer of the cyanoacrylate compound followed by a final deposition of the cyanoacrylate compound to a desired height, and a subsequent spraying of this third layer of cyanoacrylate compound with accelerator. A mechanical retentive device 52 can be embedded in the third layer of cyanoacrylate compound prior to the final accelerator spray. The cyanoacrylate compound is layered with the accelerator in order to assure complete and rapid hardening of the relatively large bulk of material forming the unbreakable die model 46 thus produced. The device 52 holds the die model 46 to an appropriate base (not shown) which is added later. By this technique, as well as by casting, unbreakable die models can be formed according to the invention. Unbreakable models so formed are particularly useful for indexing a bridge or precision partial abutment.

Figure 11:
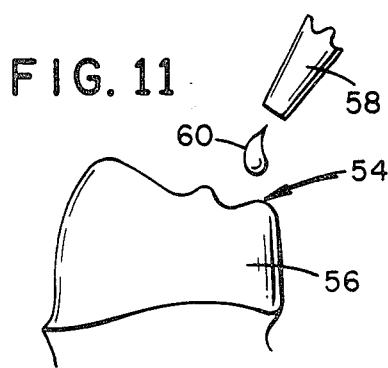
FIG. 11 is an idealized perspective view illustrating the preferred application of a cyanoacrylate compound to a die model having a missing area.
Figure 12:
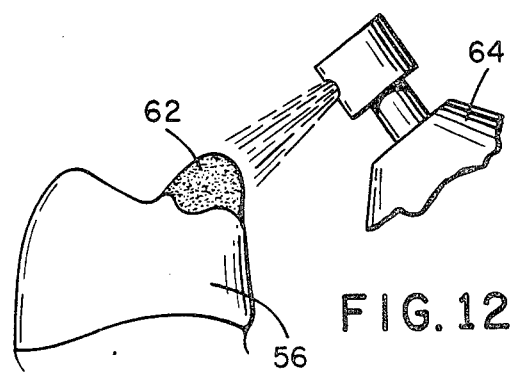
FIG. 12 is an idealized perspective view illustrating the application of an accelerator compound to a missing area which has been built up with the cyanoacrylate compound.

Referring now to FIGS. 11 and 12, a simplified illustration of physical techniques for applying the cyanoacrylate compound and the accelerator according to the invention can be seen. In FIGS. 11 and 12, the method of the invention is seen to be practiced in the build-up of the missing area of a crown preparation on a die model in order to form a more ideal shape to the model. The situation shown in FIGS. 11 and 12 is essentially that situation shown in FIG. 5. As seen particularly in FIG. 11, a mass 62 of the cyanoacrylate compound is applied to a missing area 54 of tooth model 56 through a small Teflon or polyethylene tube 58. The tube 58 can be connected to the tip of a squeezable storage bottle or similar storage container (not shown) from which the compound can be directly dispensed. The highly viscous cyanoacrylate compound can be controllably dispensed through the tube 58 as small drops 60 which can be accurately located on the missing area 54 or similar area which is to be filled in, based-up, or blocked out. Any desired quantity of the compound can be dispensed. The compound can essentially be dispensed onto the area 54 in the conformation desired for the finished product, the tip of the tube 58 being useful to shape the compound if necessary. Other implements can, of course, be used to shape the fluid compound. Once the desired quantity of the compound is properly placed on the area 54, the accelerator is sprayed onto the mass 62 of the compound, preferably from an aerosol or atomizing container such as the container 64 shown in FIG. 12. Only a relatively small amount of the accelerator is sprayed onto the cyanoacrylate compound mass 62, the quantity of accelerator being controllable such as by use of the aerosol container 64 as aforesaid or by means of a similar pump spray. Only about 1% of the accelerator to the compound by relative weight percent is typically required to rapidly harden the mass 62. On application of the accelerator, the cyanoacrylate compound immediately begins to set or cure and becomes a hardened mass within two or three minutes. Once the surface of mass 62 begins to harden, the die model can be lubricated and wax applied for sculpting of a wax tooth over the die model 56 as required for further processing. The mass 62 may be cut and shaped after hardening and before other operations are performed. The wax used for performing such additional operations cannot melt into the hardened mass 62 nor does the wax adhere substantially to the hardened mass 62. When a crown is cast in gold or other alloy and the crown is finished or polished on the die model, the heat thereby generated cannot melt the hardened mass of cyanoacrylate compound, thereby eliminating a number of vexing problems encountered in the prior art as described herein. When a large quantity of the cyanoacrylate compound is to be built up, the mass of cyanoacrylate compound can be built up in layers as described relative to FIG. 10. Alternately, the accelerator can be sprayed first on the model surface which is to receive the cyanoacrylate compound and the exposed surface of the mass 62 sprayed once the mass 62 is completely deposited.

The present invention further contemplates the addition of a dye to the cyanoacrylate compounds in order to color the base material for the purpose of providing contrast on the die model. Such a dye can be chosen from the well-known dye materials used to color cyanoacrylate compounds in other use environments. In order to prevent degradation of the cyanoacrylate compounds, the dye can be supplied separately for mixing with said cyanoacrylate compounds immediately before use.

As a further use of the cyanoacrylate compounds according to the invention, orthodontic wires can be indexed on a die model and bonded together with the cyanoacrylate base material and accelerator according to the methods previously described. The indexed wires can then be preferably soldered on the die model with advantages accruing to the present method in a similar manner as is described relative to FIG. 7.

The methods of the present invention provide advantages to the dental technician which have previously been unavailable. In particular, the invention provides methods for preparing and using a dental die model with a cyanoacrylate material which allows rapid filling of voids, basing-up of undercuts, build up of missing areas, and indexing of crowns inter alia. Use of the cyanoacrylate material provides substantial time savings and enables a less skilled technician to more rapidly and more assuredly produce a quality work product. While the invention has been explicitly described herein as embodiments which are now perceived or preferred, it is to be understood that the invention can be practiced in other forms without departing from the intended scope of the invention as defined by the appended claims.

What is claimed is:

1. A method for preparing and performing operations on a dental model, comprising the steps of:

applying a cyanoacrylate compound to the die model at necessary loci thereof, the cyanoacrylate compound being of a viscosity such that the compound will not readily flow from the location to which the compound is applied while in an uncured state; and, spraying an accelerator compound in the form of an atomized mist to the cyanoacrylate compound disposed on the dental model to thereby harden the cyanoacrylate compound.

2. The method of claim 1 wherein the cyanoacrylate compound is selected from the group consisting of ethylcyanoacrylate, methylcyanoacrylate, isobutylcyanoacrylate and n-butylcyanoacrylate.

3. The method of claim 2 wherein the accelerator compound is selected from the group consisting of N-dimethyl-p-toluidiene and the homologs thereof.

4. The method of claim 1 wherein the accelerator compound comprises an aromatic amine.

5. The method of claim 4 wherein the applying step comprises drop-wise dispensing through a tubular member of the cyanoacrylate compound to build up the quantity of the cyanoacrylate compound necessary to the preparation of the die model.

6. The method of claim 4 wherein the accelerator compound is carried by a volatile solvent.

7. The method of claim 6 wherein the volatile solvent comprises trichloroethane.

8. The method of claim 1 wherein the accelerator compound is selected from the group consisting of phenylethylethanolamine and the homologs thereof.

9. The method of claim 1 wherein the accelerator compound is carried in a trichloroethane solvent.

* * * * *